United States Patent [19]

Beller

[11] Patent Number: 5,425,580
[45] Date of Patent: Jun. 20, 1995

[54] DOSAGE FORM FOR MICRO-BUBBLE ECHO CONTRAST AGENTS

[75] Inventor: Klaus-Dieter Beller, Constance, Germany

[73] Assignee: Byk Gulden Lomberg Chemische Fabrik GmbH, Constance, Germany

[21] Appl. No.: 284,273

[22] Filed: Aug. 2, 1994

Related U.S. Application Data

[63] Continuation of Ser. No. 78,194, Jun. 21, 1993, abandoned.

[30] Foreign Application Priority Data

Dec. 28, 1990 [CH] Switzerland ............... 4132/90

[51] Int. Cl.⁶ ............................................. B01F 15/02
[52] U.S. Cl. ........................... 366/131; 366/337; 366/340; 604/82
[58] Field of Search ............ 366/349, 348, 334, 336, 366/337, 338, 339, 340, 267, 268, 262, 255, 256, 176, 131; 604/82, 83, 84, 85, 87

[56] References Cited

U.S. PATENT DOCUMENTS

| | | | |
|---|---|---|---|
| 2,477,598 | 8/1949 | Hain | 366/334 |
| 3,700,215 | 10/1972 | Hardman | 366/268 |
| 4,049,241 | 9/1977 | Taniguchi | 254/4 AC |
| 4,062,524 | 12/1977 | Brauner | 366/340 |
| 4,743,229 | 5/1988 | Chu | 604/82 |
| 4,753,536 | 6/1988 | Spehar et al. | 366/339 |
| 4,929,088 | 5/1990 | Smith | 366/337 |
| 4,969,747 | 11/1990 | Colin et al. | 366/339 |

FOREIGN PATENT DOCUMENTS

| | | |
|---|---|---|
| 0077752 | 4/1983 | European Pat. Off. . |
| 0148116 | 7/1985 | European Pat. Off. . |
| 3501331 | 7/1986 | Germany . |
| 3520772 | 12/1986 | Germany . |
| 3838530 | 5/1990 | Germany . |
| WO83/01210 | 4/1983 | WIPO . |
| WO89/08241 | 9/1989 | WIPO . |

*Primary Examiner*—Robert W. Jenkins
*Attorney, Agent, or Firm*—Jacobson, Price, Holman & Stern

[57] ABSTRACT

A dosage form for micro bubble echo contrast media which comprises a syringe (6) and a mixing chamber (1) which is connected thereto and contains a predetermined amount of gas, plus a second syringe is described. The novel dosage form allows easy, standardised preparation of echo contrast media and gives high contrast (FIG. 3).

23 Claims, 4 Drawing Sheets

DOSAGE FORM FOR MICRO-BUBBLE ECHO CONTRAST AGENTS

This application is a continuation of application Ser. No. 08/078,194, filed Jun. 21, 1993 now abandoned.

FIELD OF THE INVENTION

The invention relates to a dosage form for micro bubble echo contrast agents.

PRIOR ART

Numerous preparations which are suitable as echo contrast media and contain surface-active substances which assist with the formation of micro bubbles and stabilise them have been disclosed (for example EP-A-0 077 752). The ultrasound reflected by the micro bubbles is used to improve the ultrasonic images of cavities or vessels filled with fluid in the human and animal body. The micro bubbles are produced only just before administration of the contrast medium. For example, the contrast medium is drawn together with air or a physiologically tolerated gas into a syringe, and expelled again into a receiver vessel, several times. It is self-evident that it is not possible in this way to prepare contrast media which can be administered in a reproducible manner and which contain a defined amount of gas in micro bubbles of maximally uniform size. Attempts have therefore been made to provide the contrast medium in a syringe. Before use, the required amount of air is drawn up. Then the syringe is connected by a connector to a second, empty syringe. Vigorous pumping of the contrast medium backwards and forwards between the two syringes produces micro bubbles. However, it has emerged that the care required to obtain reasonably utilisable suspensions of micro bubbles is unacceptable in practice. In addition, a very great amount of force needs to be expended. Standardisation can scarcely be achieved in practice.

DE-A 3 838 530 describes a package for a two-component composition, which consists of two flexible containers for the two components. Before use, the two containers are connected together by a tubular adaptor which is provided in its interior with deflectors in a mutually offset arrangement. To mix the components, the contents of the containers are forced backwards and forwards through the adaptor several times.

EP-A 0 148 116 discloses a connector with two female connecting pieces for two syringes to be inserted. The channel through the connector has a constriction which is intended to assist turbulent flow of the fluid which is pumped backwards and forwards between the two syringes.

U.S. Pat. No. 4,049,241 discloses a mixing chamber for fluid materials, in which a plurality of rod-like mixing elements are provided in a tubular housing and are inclined with respect to the axis of the tube.

SUMMARY OF THE INVENTION

The invention has an object of providing apparatus for preparing a dosage form for echo contrast media which permits the user to administer the micro bubble echo contrast media in a standardised and optimised manner without unacceptable effort. Another aim of the invention is to improve the quality of the images of body structures obtainable with a micro bubble echo contrast medium and to improve the reproducibility of the images.

Another aim of the invention is to increase the safety of use by avoiding the production of gas bubbles which, because their diameter is too large, expose the patient to the risk of embolism.

Another aim of the invention is to avoid a risk of infection.

These objects are achieved according to the invention by the apparatus for preparing a dosage form for echo contrast media comprising a syringe and a mixing chamber which is unreleasably connected thereto and contains a predetermined amount of gas, plus a second syringe.

The invention therefore relates to apparatus for preparing a dosage form for micro bubble echo contrast media comprising a first syringe and a mixing chamber which is unreleasably connected thereto and contains a predetermined amount of gas, plus a second syringe. Further subject-matter is evident from the patent claims. The invention further relates to a syringe for echo contrast media, which is characterised in that it is unreleasably connected to a tubular mixing chamber which has mixing elements in its inner lumen.

The mixing chamber is preferably tubular and has mixing elements in its inner lumen.

In a preferred embodiment, the mixing elements are designed in the form of spikes, that is to say the mixing elements preferably stand at right angles to the inner wall of the mixing chamber and thus point in the direction of the long axis of the mixing chamber tube. It is expedient to design the mixing elements with sharp edges in the direction of the syringe barrel, that is to say to produce separation edges. There is preferably a mutually offset helical arrangement of the mixing elements. Additional separation edges can be achieved by one or more perforated diaphragms.

Echo contrast media which are in the form of a homogeneous solution are, according to the invention, provided in a syringe or drawn up air-free into a syringe from a storage container such as, for example, an ampoule, before use. The syringe is then connected to the free end of the mixing chamber which is firmly connected to a syringe and whose interior volume contains the predetermined amount of gas. The echo contrast medium is pumped through the mixing chamber into the second, empty syringe and subsequently back again into the first syringe. A relatively stable micro bubble suspension has been formed after only a few repetitions of the pumping process. The echo contrast medium is now ready for administration. The user now replaces the empty syringe by an injection needle and injects the contrast medium. It is expedient to inject from the syringe with mixing chamber because in this case injection directly entails passage through the mixing chamber once more.

The syringe with mixing chamber is produced by processes known to the person skilled in the art out of materials customary for such medical articles. For example, the mixing chamber is produced by the injection moulding process and connected unreleasably to the connecting piece of a conventional syringe, for example by adhesive or ultrasonic welding or is produced from the outset in one piece together with the syringe barrel. The free end of the mixing chamber can have the form of a male or female connecting piece. In the case where the free end is designed as male connecting piece, the second syringe has a female connecting piece, or an adaptor with two female connectors is fitted on the male connecting piece of the second syringe. In the case where the free end is designed as female connecting piece, the injection needle is fitted via an adaptor with two male connecting pieces.

It has emerged that the second syringe can be dispensed with when the formation of stable micro bubbles of suitable size is possible with relatively low energy expenditure with the echo contrast medium formulations used. In favourable cases, even the single passage through the mixing chamber on injection suffices to form micro bubbles whose quality and amount are adequate. This procedure is expedient, for example, in investigations of the right ventricle.

The dosage form according to the invention for micro bubble echo contrast media is preferably provided in a set ready for use. If the echo contrast medium consists of a single liquid component, the latter can be, for example, contained in a normal syringe or present in a vial from which it is drawn up air-free into the syringe. The preset amount of gas to be dispersed is located in the mixing chamber. It has proved to be expedient to choose the free interior volume of the mixing chamber such that it corresponds to the volume of the predetermined amount of gas which yields an optimal micro bubble echo contrast medium with the contrast medium components. The connecting pieces of the two syringes are closed with appropriate caps or stoppers. It is expedient to provide the said parts together with an injection needle and, if required, with further aids customary for i.v. use, such as alcohol swab and plaster dressing, sterile in a pack, for example a conventional blister pack.

Suitable contrast medium components are those compositions which yield sufficiently stable micro bubbles on foaming with gases for ultrasonic investigations. The components contain surface-active substances and, if required, further substances promoting the stabilisation of micro bubbles, such as, for example, substances which increase the viscosity. Suitable components are described, for example in EP 0 077 752 and EP 0 212 568.

The dosage form according to the invention for micro bubble echo contrast media contains 1 to 20 ml, preferably 2 to 8 ml, and particularly preferably 5 ml, of liquid contrast medium component. The dosage form according to the invention contains 0.01 to 0.1, preferably 0.04 to 0.06 ml of gas per 1 ml of liquid contrast medium component.

A preferred embodiment of the dosage form according to the invention comprises two syringes with an inner volume of 5 ml, of which one is unreleasably connected to a mixing chamber which has an inner volume of 0.18 ml. The syringe which is unreleasably connected to the mixing chamber is empty. The mixing chamber contains 0.18 ml of gas, preferably sterile air, and is closed by either a stopper or a cap. The second syringe contains 3 ml of a liquid contrast medium component. This syringe is also closed by a stopper or cap.

The invention is to be explained in more detail hereinafter by means of FIGS. 1 to 4.

Figure 1:
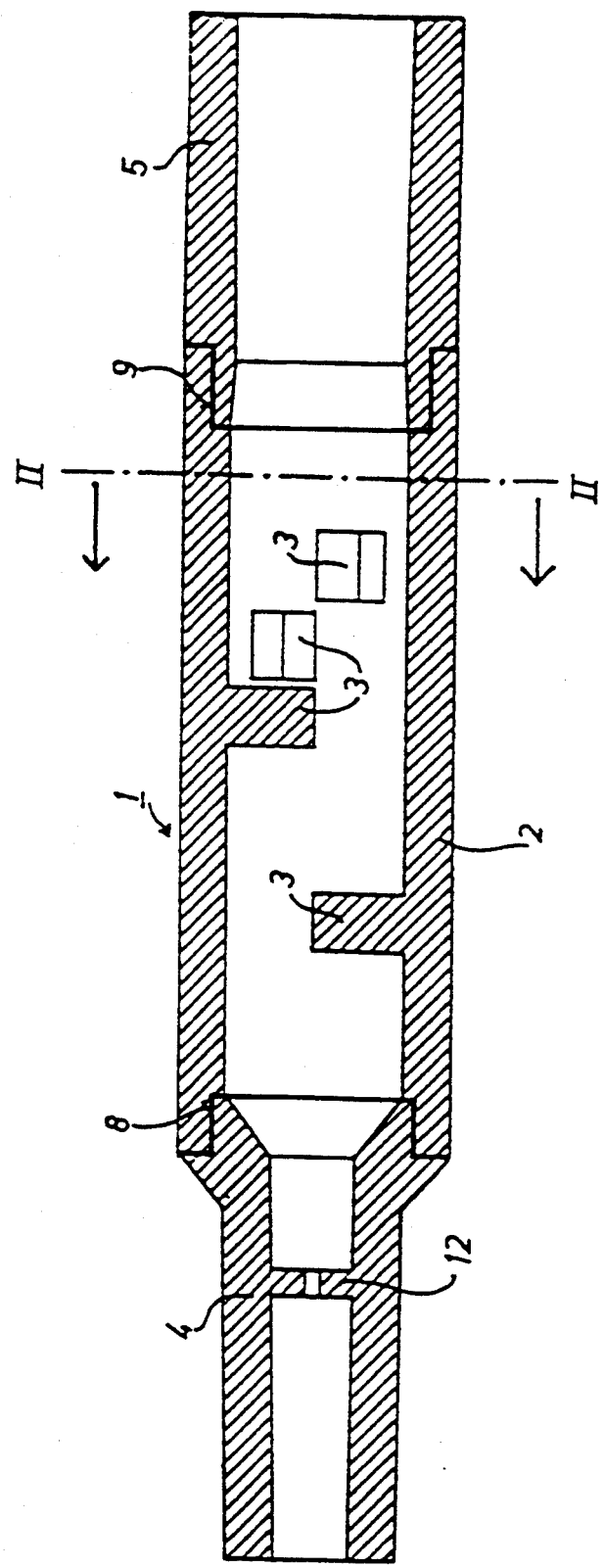
FIG. 1 shows a longitudinal section through a mixing chamber.

FIG. 1 depicts an embodiment of the mixing chamber 1 in longitudinal section. The cylindrical tubular sleeve 2 has mixing elements 3 which stand at right angles to its interior wall and have a mutually offset helical or spiral arrangement. A connecting piece is shaped at the left-hand end and is designed as male Luer connection. A connecting piece 5 is shaped on the right-hand end and is designed as female Luer connection. It appears expedient, for reasons of production technique, to fabricate the mixing chamber from three parts, that is to say from the tubular sleeve 2 with the mixing elements 3 and the two connecting pieces 4, 5 and to connect in a suitable manner. The connection lines are designated 8 and 9 in FIG. 1. The connecting piece 5 can be directly replaced by a corresponding connecting part of a piston syringe. As mentioned hereinbefore, the connecting piece 4 can also be in the form of a female Luer connection. If required, a perforated diaphragm 12 is provided in the connecting piece 4. An intensification of the dispersion can be achieved by this optional perforated diaphragm 12.

Figure 2:
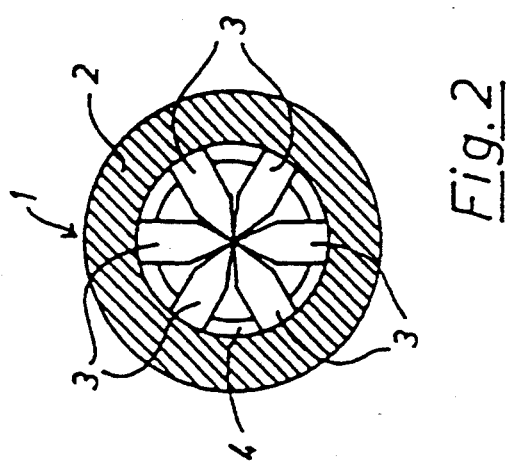
FIG. 2 shows a cross-section through a mixing cheer along the line II in FIG. 1.

FIG. 2 shows a cross-section through a mixing chamber along the line II in FIG. 1. The mixing elements 3 in the form of spikes standing at right angles on the inner wall of the tubular sleeve 2 are seen.

Figure 3:
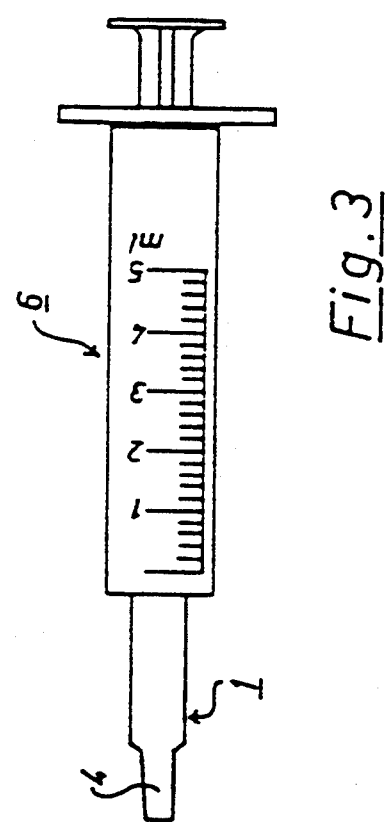
FIG. 3 shows a side view of a syringe with mixing chamber.

FIG. 3 depicts a syringe 6 with mixing chamber 1 with male connecting piece, where the mixing chamber 1 is directly shaped on the base of the syringe barrel.

Figure 4:
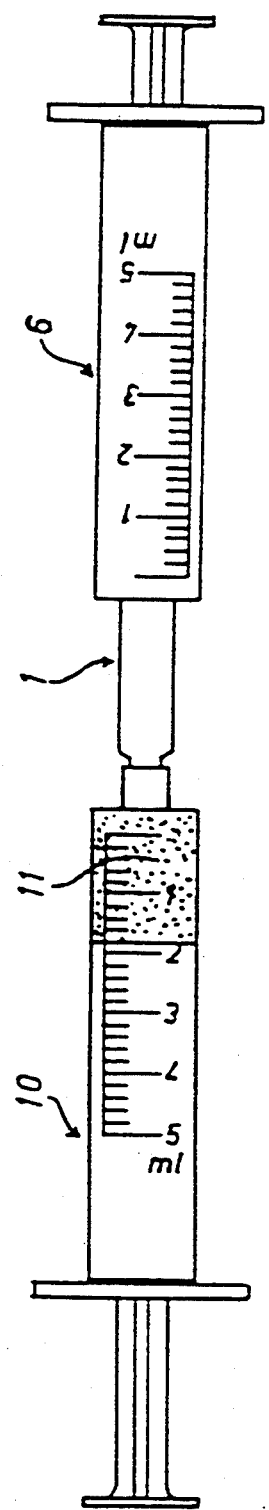
FIG. 4 shows a side view of a syringe with mixing chamber with second syringe attached.

FIG. 4 shows the syringe 6 with mixing chamber 1 which is shaped on and onto whose male connecting pieces is fitted a second syringe 10 which contains the echo contrast medium 11. The amount of gas required for the micro bubbles is contained in mixing chamber 1. The micro bubble suspension ready for administration is prepared by pumping the echo contrast medium 11 backwards and forwards between syringe 10 and syringe 6 through mixing chamber 1.

The dosage form according to the invention achieves increased safety of use. It should be particularly emphasised in this connection that, owing to the predetermined amount of gas, exactly the amount of gas which is optimally suited to the composition and amount of the liquid component is used, and thus leads to a maximum information content of the obtainable images. Errors which may arise through conventional drawing up of too much or too little gas are reliably avoided thereby. In particular, the drawing up of too much gas might result in a risk of embolism for the patient. However, even the drawing up of too little gas in the conventional method may make repetition of the investigation necessary because of deficient imaging. In addition, the risk of infection for the patient is considerably reduced by the dosage- form according to the invention because, in contrast to the drawing up of ambient air which has been hitherto customary, sterile gas is used and no ambient air which may be contaminated with resistant hospital organisms enters the blood circulation of the patient via the micro bubbles. An additional factor is that connection procedures are avoided, owing to the unreleasable connection between mixing chamber and syringe, with regard to possible intrusion of organisms.

The safety of use is also greatly improved by the possibility now of considerably reducing the number of backward and forward pumping procedures, while there is a simultaneous increase in the quality of the micro bubble suspension. Since, in addition, the force expenditure necessary for the pumping backwards and forwards is considerably reduced, there is an increased readiness of the user to carry out the foaming procedure in accordance with the instructions until the state of the micro bubble echo contrast medium is optimal for the intended purpose.

The dosage form according to the invention results in micro bubble suspensions which are distinguished by a surprising improved quality of contrast.

In addition, it has been observed that, after disappearance of the contrast from the lumen of the body cavities investigated, the inner surfaces of the body cavities surprisingly remain readily visible for a substantial period. For example, this marking of surfaces, which has to date been observed only with dosage forms according to the invention, is outstandingly suitable for diagnosis of the heart. It appears that the presentation according to the invention favours the formation of micro bubbles adhering to interior body surfaces.

In a comparative test, 3 ml samples of an infusion solution containing crosslinked polypeptides (Haemaccel ® supplied by Behringwerke), which is suitable for the preparation of micro bubble contrast media, were pumped backwards and forwards together with 0.18 ml of air, on the one hand five times between two syringes connected by a three-way tap (test A), and on the other hand five times in a dosage form according to the invention between the syringe connected to a mixing chamber and a syringe attached to the mixing chamber (test B). Subsequently formulations A and B were administered i.v. to conscious dogs. Echocardiography of the right ventricle was carried out with a Sonoscope 4 at 3.5 MHz. The resulting video printouts were evaluated by densitometry. The densitometer (Gretag D182) measures changes in the brightness in the range from 0.00 to 2.50 DU (density units) in 100 steps. The calibration is based on the calibration card which is provided by the manufacturer and complies with DIN 16536 (calibration reference), where the brightest white is assigned the value 1.64 and the darkest black is assigned the value 0.00. The value for each animal is determined from the mean of four individual measurements within a square centimetre.

The following results were obtained:

|  | Contrast quality | maximum intensity | 10 sec after administration | 20 sec after administration |
| --- | --- | --- | --- | --- |
| Test A | poor | 1.06 | 0.39 | 0.19 |
| Test B | good | 1.56 | 1.09 | 0.58 |

It is evident, that in addition to the easier and safer use, the dosage form according to the invention results not only in a considerably improved contrast quality but also in a surprising increase in intensity, and the qualitatively and quantitatively superior contrast is in fact observable for very much longer too.

The novel dosage form for micro bubble echo contrast media not only simplifies the manipulation of echo contrast media and increases safety on use but, in particular, achieves a considerable additional gain in diagnostic information.

I claim:

1. A combination of a) means for generating micro bubbles in an echo contrast medium with b) a mixing chamber and c) a predetermined amount of sterile gas, wherein the means is a syringe which has an outlet sealed to the mixing chamber which contains the predetermined amount of sterile gas.

2. A combination of claim 1 wherein the mixing chamber has an inner lumen in which the predetermined amount of sterile gas is contained.

3. A combination of claim 2 wherein the mixing chamber is tubular and comprises a plurality of mixing elements in the inner lumen.

4. A combination of claim 3 wherein the mixing elements are in the form of spikes.

5. A combination of claim 3 wherein the mixing elements are in a mutually offset helical arrangement.

6. A combination of claim 3 wherein the mixing chamber comprises one or more perforated diaphragms.

7. A set which is useful for applying micro-bubble echo contrast media and which comprises:
   a) a combination of claim 1,
   b) a second syringe,
   c) echo contrast medium, and
   d) optionally, another container;
the echo contrast medium being contained in the second syringe or in the other container.

8. Apparatus useful for preparing micro bubble echo contrast media and comprising a first syringe, a mixing chamber and a second syringe; the mixing chamber having an inlet, an outlet, an inner lumen and a predetermined amount of sterile gas in the inner lumen; the first syringe comprising a barrel and having an outlet sealed to the inlet of the mixing chamber; and the second syringe having an outlet means for connecting it to the outlet of the mixing chamber.

9. Apparatus according to claim 8, wherein the mixing chamber has mixing elements in the inner lumen.

10. Apparatus according to claim 9, wherein the mixing elements are in the form of spikes.

11. Apparatus according to claim 10, wherein the mixing elements have sharp edges in the direction of the syringe barrel.

12. Apparatus according to claim 9, wherein the mixing elements are in a mutually offset helical arrangement.

13. Apparatus according to claim 9, wherein the mixing chamber comprises one or more perforated diaphragms.

14. Apparatus according to claim 8, wherein the first syringe and the mixing chamber are fabricated from plastic.

15. Apparatus of claim 8 wherein the outlet means of the second syringe is directly connected to the outlet means of the mixing chamber.

16. Apparatus according to claim 15, wherein the second syringe contains a liquid contrast medium component.

17. Apparatus useful for preparing micro bubble echo contrast media and comprising a first syringe, a mixing chamber and a second syringe; the mixing chamber having an inlet, an outlet, one or more perforated diaphragms, an inner lumen and a plurality of mixing elements in the inner lumen; the first syringe comprising a barrel and having an outlet sealed to the inlet of the mixing chamber; and the second syringe having outlet means for connecting it to the outlet of the mixing chamber.

18. Apparatus of claim 17 wherein the outlet means of the second syringe is directly connected to the outlet of the mixing chamber.

19. Apparatus of claim 18 wherein the first syringe and the mixing chamber are fabricated from plastic.

20. Apparatus useful for preparing micro bubble echo contrast media and comprising a first syringe, a mixing chamber and a second syringe; the mixing chamber having a inlet, an outlet, an inner lumen and a plurality of mixing elements, in the form of spikes, in the inner lumen; the first syringe comprising a barrel and having an outlet sealed to the inlet of the mixing chamber; and the second syringe having outlet means for connecting it to the outlet of the mixing chamber.

21. Apparatus of claim 20 wherein the mixing elements have sharp edges in the direction of the syringe barrel.

22. Apparatus useful for preparing micro bubble echo contrast media and comprising a first syringe, a mixing chamber and a second syringe; the mixing chamber having an inlet, an outlet, an inner lumen and a plurality of mixing elements, in a mutually offset helical arrangement, in the inner lumen; the first syringe comprising a barrel and having an outlet sealed to the inlet of the mixing chamber; and the second syringe having outlet means directly connected to the outlet of the mixing chamber.

23. Apparatus useful for preparing micro bubble echo contrast media and comprising a first syringe, a mixing chamber and a second syringe; a mixing chamber having an inlet, an outlet, an inner lumen and a plurality of mixing elements in the inner lumen; the first syringe comprising a barrel and having an outlet sealed to the inlet of the mixing chamber; and the second syringe containing a liquid contrast medium component and having outlet means directly connected to the outlet of the mixing chamber.

* * * * *